United States Patent [19]
Constantine

[11] Patent Number: 5,603,946
[45] Date of Patent: Feb. 18, 1997

[54] WOUND DRESSING

[75] Inventor: Barry Constantine, Island Heights, N.J.

[73] Assignee: Bristol-Myers Squibb Company, Skillman, N.J.

[21] Appl. No.: 134,152

[22] Filed: Oct. 8, 1993

[51] Int. Cl.$^6$ .................................................. A61F 13/00
[52] U.S. Cl. ........................................... 424/445; 424/443
[58] Field of Search ................................. 424/443, 445, 424/448

[56] References Cited

U.S. PATENT DOCUMENTS

| | | | |
|---|---|---|---|
| 1,920,808 | 8/1933 | Sander | 128/154 |
| 2,273,873 | 2/1942 | Klein | 602/55 |
| 3,888,247 | 6/1975 | Stenvall | 128/155 |
| 4,231,357 | 11/1980 | Hessner | 602/55 |
| 4,399,816 | 8/1983 | Spangler | 128/154 |
| 4,638,796 | 1/1987 | Sims | 128/155 |
| 4,649,909 | 3/1987 | Thompson | 128/156 |
| 4,909,243 | 3/1990 | Frank et al. | 128/156 |
| 4,917,112 | 4/1990 | Kalt | 602/55 |
| 5,056,510 | 10/1991 | Gilman | 128/155 |
| 5,086,763 | 2/1992 | Hathman | 602/55 |
| 5,086,764 | 2/1992 | Gilman | 602/42 |
| 5,090,406 | 2/1992 | Gilman | 602/52 |
| 5,106,362 | 4/1992 | Gilman | 602/47 |
| 5,167,613 | 12/1992 | Karami et al. | 602/52 |
| 5,244,457 | 9/1993 | Karami et al. | 602/55 |
| 5,308,313 | 5/1996 | Karami et al. | 602/55 |

FOREIGN PATENT DOCUMENTS

| | | |
|---|---|---|
| 1187364 | 5/1985 | Canada . |
| 2175208 | 11/1986 | United Kingdom . |
| 93/07841 | 4/1993 | WIPO . |
| 94/06382 | 3/1994 | WIPO . |

*Primary Examiner*—Jyothsna Venkat
*Attorney, Agent, or Firm*—Theodore R. Furman, Jr.; John M. Kilcoyne

[57] ABSTRACT

A novel two piece dressing having a baseplate and wound fluid absorbing material is provided according to the present invention. The baseplate is provided with slits or incisions for covering, examining and/or treating the wound without removing the baseplate. The dressing contains an absorbent material designed to remove excess exudate from the wound through an aperture in the baseplate. The incisions or slits may, in one embodiment, extend from the aperture and define one or more flaps for viewing and/or treating the wound.

13 Claims, 2 Drawing Sheets

WOUND DRESSING

FIELD OF THE INVENTION

The present invention relates to a wound dressing that is useful for the treatment of wounds and particularly concerns a dressing especially suitable for decubitus and in particular leg ulcers.

BACKGROUND OF THE INVENTION

In connection with the care and treatment of wound it is preferable that the selection and the design of a wound dressing focus on the specific requirement of the particular wound itself. The term wound is meant to include burns, pressure sores, punctures, ulcers and the like. A critical aspect of wound care is consideration of the requirements of the epithelium i.e. that area of new cell growth directly peripheral to the wound which is formed during the healing process so that healing is facilitated. Another consideration in wound treatment albeit of a somewhat lesser concern are the needs of the surrounding unwounded skin.

Since it is recognized that healing of the wound occurs in the epithelium by cell growth from the periphery inward, care is taken not to unnecessarily damage or irritate this new area of growth. Frequently, with prior art dressings, problems can occur during dressing changes particularly where the dressing adheres to the epithelium or where the granulation tissue and new cell growth becomes intertwined within the matrix of the dressing. In both instances, there is a risk that removal of the dressing will damage the sensitive tissue thereby causing a regression in progress of wound healing. Another concern in the selection of wound dressing is to provide a dressing that maintains a moist environment and prevents scab formation.

At least a portion of the area of the skin around the wound that has not been damaged by the wound is in contact with the wound dressing. For example, a significant portion of the surrounding skin may be covered for extended periods with the adhesive or a wrap which secures the dressing in position. The unwounded skin may be irritated by the dressing. This is particularly a problem with ulcers specifically leg ulcers where the surrounding skin can easily become sensitized by strong medicaments and such wounds are frequently accompanied with flaking, and/or scaling of the surrounding tissues or eczema.

Another factor in wound care is the frequency of dressing changes. The above are all considerations in the timing of dressing change. In addition, it is desirable to change dressing more frequently where the wound is emitting a large volume of exudate. Thus, considering the various types of wound, the numerous dressings that are available, and the various stages of healing, there is a need for a dressing that aids in monitoring the healing of the wound.

In the area of leg ulcers one type of treatment presently used comprises the application of gauze to the ulcer and the utilization of a compression wrap to secure the gauze to the ulcer. Since the gauze quickly becomes saturated, frequent changes are necessary and damage to the epithelium and surrounding skin may occur. If the gauze is left on for too long a period, the exudate which contains proteolytic enzymes can begin to digest the patient's surrounding skin.

A second type of treatment is the Unna's Boot (commercially available from Biersdorf, Inc.) which comprises a zinc paste-containing bandage wrapped around the patient's leg from above the toes to below the knee. Other Unna's Boot/zinc impregnated treatments are available from Miles and Graham Field. This dressing is typically left in place for a week at a time and absorbent pads must be applied to the outside of the dressing in the area of the ulcer to absorb excess exudate. Seepage of exudate throughout the wrap is common, however, and damage to the skin and epithelium is inevitable.

Another type of dressing is disclosed in U.S. Pat. No. 5,106,362 to Gilman. This dressing is provided with a base sheet for contacting the skin of the patient. The base sheet has an opening for placement over the wound. The dressing has a vent for providing controlled leakage of fluid along a path from the wound through the opening of the base sheet. The vent is designed to provide control over wound leakage along a "tortuous path" from the wound through the opening of the base sheet.

A modification of the dressing of U.S. Pat. No. 5,106,362 is disclosed in U.S. Pat. No. 5,056,510 also to Gilman. The '510 patent discloses a vented dressing where the fabric reservoir for wound exudate is contained within a chamber. The walls of the chamber are intended to provide a barrier to bacteria and other contaminants. The walls of the chamber are intended to be air permeable so as to permit egress of air from the voids of the fabric reservoir.

U.S. Pat No. 4,909,243 to Frank which is owned by the assignee of the present invention discloses a two piece wound dressing comprising a baseplate having an adhesive surface for contacting surrounding skin. The baseplate has an aperture extending completely through the baseplate and around the wound over which a wound pad of a desired wound dressing material can be placed. This patent provides an aperture that permits visualization of the wound but does not permit reapplication of the dressing over the wound.

Although the prior art wound dressings provide a tortuous path for exudate to an absorbent material, there is a need for a wound dressing that not only provides superior exudate absorption but also a dressing that permits access to, as well as visual inspection of the wound.

SUMMARY OF THE PRESENT INVENTION

In accordance with the present invention there is provided an improved wound dressing. The dressing comprises an adhesive baseplate which contacts the wound and surrounding skin and an absorbing means overlying the baseplate. The baseplate has slits which define one or more flaps such that when the flaps are lifted away from the wound a first aperture generally the size and shape of the wound is defined. The first aperture facilitates examining and/or treating the wound without removing the baseplate thereby avoiding damage to the wound epithelium. The flaps can thereafter be closed back over the wound. The baseplate further includes a second aperture substantially smaller than the size of the wound when the one or more flaps are closed. The second aperture facilitates removal of excess wound exudate to the overlying absorbent means. The wound dressing of the present invention provides superior wound care in that dressing changes, i.e., changes of the absorbent material, can be made while reducing the risk of damaging delicate healing skin peripheral to the wound. This is possible because the baseplate can remain positioned on the surrounding healthy skin and maintain protection for the wound surface for extended periods of time.

DETAILED DESCRIPTION OF THE INVENTION

Figure 1:
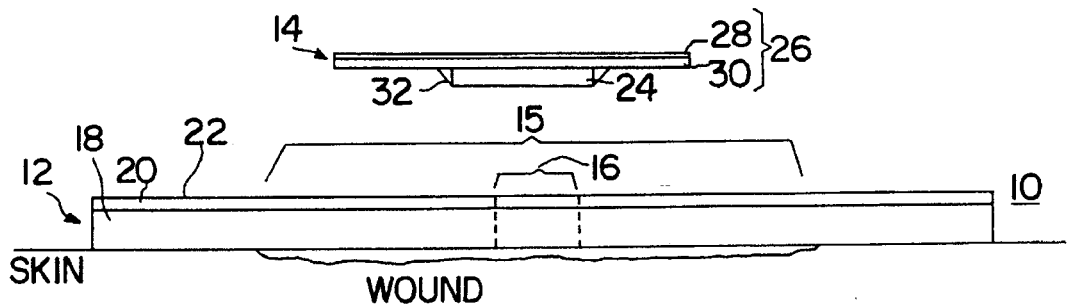
FIG. 1 is a cross sectional view of a baseplate of the dressing of the present invention.

Referring to FIG. 1, an embodiment of the wound dressing 10 of the present invention is shown to have a base plate 12 and a wound pad 14, wherein the baseplate includes a first aperture (not shown, but designated by the arrows 15) which first aperture 15 is closed in this FIG. 1, and a second aperture 16 which extends through the baseplate 12. The wound pad 14 is designed to fit over, and optionally can fit into, the second aperture 16. The first aperture 15 typically corresponds to the size and shape of a wound (not shown). Also, the first aperture 15 may be round, oval, square, rectangular or some other suitable shape as desired for the particular wound. It should be noted, as will be described in greater detail below, that when the wound pad 14 is secured over the baseplate 12 and second aperture 16 in actual use, the first aperture 15 is closed. This provides a great therapeutic benefit in that the second aperture 16 provides a non-tortuous, facile path for removal of excess wound exudate. In a closed position, nearly all of the wound area is in contact with the hydrocolloid adhesive 18 of the baseplate 12 since the aperture 15 need only be opened for examination or treatment.

The baseplate comprises an adhesive layer 18 which is designed to contact the skin and a backing layer 20 with upper surface 22 which overlies the adhesive layer 18. The backing layer is preferably a suitable polymeric material. Although the invention is described herein in terms of a wound pad 14, it should be understood that any absorbent means can be utilized in place of the present wound pad 14.

The wound pad 14 is preferably releasably and optionally resealably adhered to the upper surface 22 of the backing layer 20 of baseplate 12. The wound pad 14 comprises a dressing element 24 adhered to a top layer 26 which in turn may comprise a second backing layer 28. A second adhesive 30 can serve as the releasable, resealable adhesive means and should be able to release from the upper surface 22 of the baseplate 12 substantially more easily than the first adhesive layer 18 releases from the skin of the patient. If the optional second adhesive layer 30 is not present alternate means known in the art for releasably adhering the wound pad 14 to the baseplate 12 should be provided. Examples of suitable baseplate and wound pads are described in U.S. Pat. No. 4,909,243 the disclosure of which are incorporated herein by reference.

Figure 2:
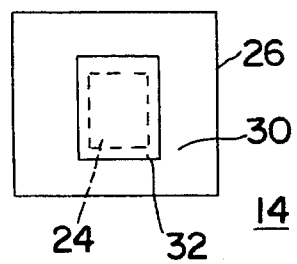
FIG. 2 is a view of the wound contact surface of the wound pad of the present invention.
Figure 3:
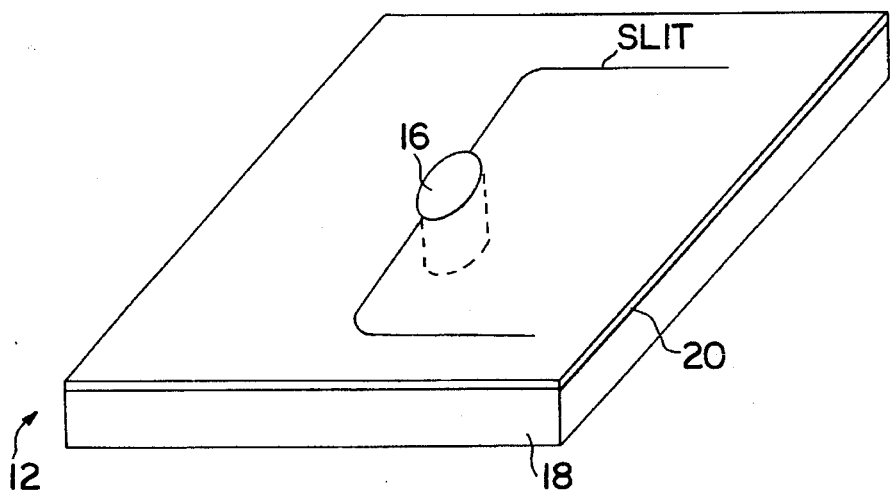
FIG. 3 is a perspective view of a baseplate of the present invention.

In a preferred embodiment the wound pad 14 as shown in FIGS. 1 and 2 comprises a dressing element 24 adhered to an adhesive layer 30 (having an optional backing layer 28) wherein the adhesive layer 30 is larger in dimension than the dressing element 24. Preferably, a non-stick surface 32 can be provided on the wound-facing surface of the dressing element 24 in any convenient manner. One way of accomplishing this is shown in FIG. 2 which depicts the wound-facing surface of the wound pad 14. It can be seen that the adhesive layer 30 is larger than the dressing element 24 and the non-stick surface 32. This provides that the peripheral adhesive 30, i.e., the adhesive beyond the non-stick surface, can secure the wound pad 14 to the baseplate 12 when in use. Further, the non-stick surface 32 is larger than the dressing element 24. Thus, the overlapping portion of the non-stick surface 32 secures the dressing element 24 to the adhesive layer 30. This novel wound pad 14 is considered an integral part of the present invention along with the novel baseplate 12 described below.

The adhesive layer 18 comprises an adhesive mass of adhesive material. Fluid interactive adhesives known in the art for the treatment of wounds which emit exudate, are preferred and they typically comprise hydrocolloids dispersed in a polymer matrix. Also, the adhesive material for the baseplate is preferably capable of adhering to moist surfaces. Adhesive compositions known in the art for use in ostomy skin barriers and male incontinence applications are especially well-suited for the baseplate of the present invention.

For example, Chen in U.S. Pat. No. 3,339,545 discloses an adhesive comprising a blend of one or more water soluble or water swellable hydrocolloids and a viscous substance such as polyisobutylene. A film of water insoluble material, corresponding to the backing layer in the instant case, is affixed to one surface of the adhesive. The article is commercially available as Stomahesive ™ and Durahesive from Convatec.

Doyle et al. in U.S. Pat. No. 4,551,990 discloses a pressure sensitive adhesive suitable for medical purposes comprising 5 to 30 percent by weight of one or more polyisobutylenes or a blend of one or more polyisobutylenes and butyl rubber, 3 to 20 percent by weight of one or more styrene radial or block type copolymers, 8 to 40 percent by weight of mineral oil, 15 to 65 percent by weight of one or more water soluble hydrocolloids gums, up to 15 percent by weight of one or more water swellable cohesive strengthening agents provided that the hydrocolloid gums and strengthening agents together are present in an amount of between about 15 and 65 percent by weight, and 7.5 to 15 percent by weight of a tackifier.

Pawelchak et al., in U.S. Pat. No. 4,393,080 discloses an adhesive composition comprising 30 to 70 percent by weight of a pressure sensitive viscous adhesive material and an optional thermoplastic elastomer. The pressure sensitive material is selected from natural rubber, silicone rubber, acrylonitrile rubber, polyurethane rubber and polyisobutylenes. The elastomer can be medium molecular weight polyisobutylenes, butyl rubber or styrene copolymers. This adhesive material further includes 3 to 60 percent by weight of material or synthetic polymers capable of developing elastomeric properties when hydrated which can be gluten and long chain polymers of methyl vinyl ether/maleic acid.

Preferred for the adhesive layers 18 and 30 are the Doyle et al. adhesives such as those commercially available as Durahesive or DuoDerm CGF®. While the above adhesives are well suited for use in the baseplate 12 of the present invention, they are merely meant to be exemplary and any skin compatible adhesive could be employed, with the fluid interactive adhesive preferred.

In one embodiment the adhesive material of the baseplate 12 may further include between 2 and 20 percent and preferably about 10 percent by weight of zinc oxide. The zinc oxide not only aids in the care of the skin surrounding the wound, but fluid interactive adhesive materials become more pliable with the zinc oxide included.

The first backing layer 22 of the baseplate 12 can be of any polymer film, nonwoven material, weave or the like, or combination thereof, known in the art, with flexible polyurethanes silicone coated polymers and embossed polyethylene films preferred.

The dressing element 24 of the wound pad 14 can also be of any convenient material or materials used as wound dressing in the wound care art. Typical materials include, but are not limited to, natural and synthetic polymeric absorbents, hydrocolloid/polysaccharide absorbents, cellulosic absorbents, gum and resin absorbents, inorganic absorbents, gel-forming fluid-interactive adhesive dressings, wool, cotton, lint and superabsorbents, i.e. water swellable polymers typically in the form of fiber or flock material. The structure of the dressing element 24 may comprise a complete laminated dressing, e.g. that described by Pawelchak et al. in U.S. Pat. No. 4,538,603 wherein an occlusive dressing commercially available from Convatec known as Duoderm ™ is disclosed. Pawelchak et al. describe dressings comprising an adhesive layer of a gel-forming fluid interactive adhesive, a layer of semi-open cell polymeric foam and/or a polymeric film backing layer. The dressing may also include a second adhesive layer designed to enhance cohesion. Also U.S. Pat. No. 4,793,337, describes a dressing similar to the double adhesive structure of Pawelchak but which also includes a layer of calcium alginate wool or fiber interposed the adhesive layer. Any other pad, gauze or wound film known in the art, e.g., materials from the diaper and incontinence arts, can be utilized as the dressing element 24. Specific suitable dressing include Sunbeam Process absorbent materials (Gelman Technology), the Composite Air Laid Superabsorbent Pad (Dry Forming Processes) and Polysteen Superabsorbent Fiber Flock SAFF (Hanfspinnerei Steen & Co.). Most preferred for the dressing element 24 is a fibrous matrix of absorbent and/or superabsorbent materials. A cellulose matrix containing a superabsorbent, e.g., carboxymethylcellulose, is preferred. One such suitable matrix is Salsorb®.

These and various other wound dressings are suitable for use as the dressing element 24 in the wound pad 14 of the wound dressing of the present invention. Regardless of the material chosen, the dressing element 24 should be capable of handling the wound fluids so as to protect the wound and surrounding areas form the deleterious effects thereof. This is accomplished by the dressing element's ability to remove or "wick" the fluids away from the wounds.

The second backing layer 28 can be chosen from the same materials as the first backing layer 20 and can be the same as, or different than, the first backing layer 20. A preferred second backing layer is a spun laced polyester nonwoven (e.g. Kendall's Novenette) bonded to a polyester film.

As mentioned above, when the dressing element 24 is a gauze or composite pad, it may further include an overwrap, e.g. a polyester nonwoven overwrap (e.g., those available from Kendall, Fasson, Semex and the like) and a non-adherent facing as is known in the art.

Figure 4A:
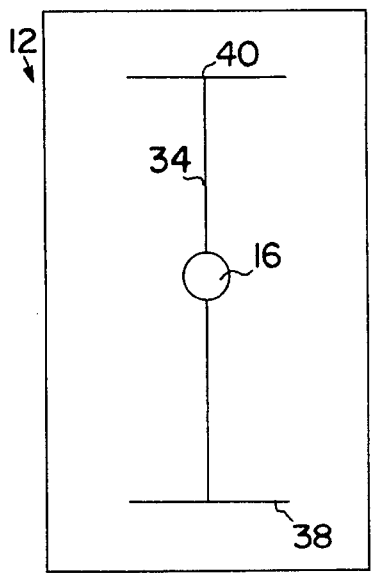
FIG. 4A is a top view of a dressing of the present invention.
Figure 4B:
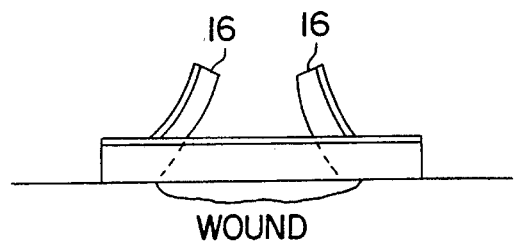
FIG. 4B is a side view of the dressing of FIG. 4A.

As shown in FIG. 4A the baseplate 12 is provided with a pair of incisions or slits extending from aperture 16 along the surface of the baseplate. These incisions or slits extend from the upper surface 22 of the baseplate 12 through the adhesive mass 18. In one embodiment the incisions 34 and 36 may each be further provided with an incision 38 and 40 on their ends opposite aperture 16. The incisions 38 and 40 are approximately at right angles to incisions 34 and 36 in FIG. 4A, however, other angles can be selected depending on the shape of the wound being treated. Similarly, the path of incisions 34 and 36 can vary from the configuration shown in FIG. 4A depending on the shape of the wound. Thus, while shown in FIG. 4A as being relatively straight lines these slits or incisions can have virtually any shape depending on the wound.

The purpose of the slits or incisions is to facilitate visualizing the wound's healing progress. When the flap is lifted an aperture which approximates the size of the wound is provided thus permitting complete visualization and wound access. When the flap is restored to its original position the remaining aperture 16 provides for the free flow of wound exudate to the absorbent means or wound pad 14. The exudate accordingly passes directly from the wound area through the aperture to the absorbent pad 14 thus providing a non-tortuous path for the exudate.

Figure 5A:
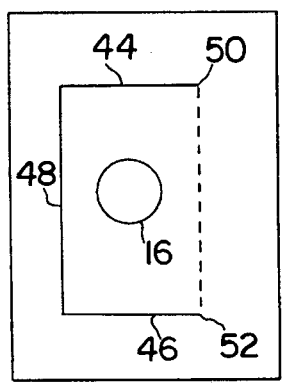
FIG. 5A is a top view of an alternate embodiment of the dressing of the present invention.
Figure 5B:
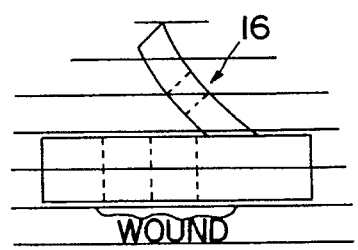
FIG. 5B is a side view of the dressing of FIG. 5A.

After observing the progress of the wound healing the raised edges of the slits are released. The wet hydrocolloid edges of the dressing may adhere and seal leaving only aperture 16. As shown in FIGS. 5 and 6 the incisions may take a variety of configurations. FIGS. 5A and 5B show a generally rectangular shaped incision having a pair of incisions 44 and 46 extending from incision 48. The axis of the fold is the imaginary line extending from the terminating point 50 on incision 44 to the terminating point 52 on incision 46.

Figure 6A:
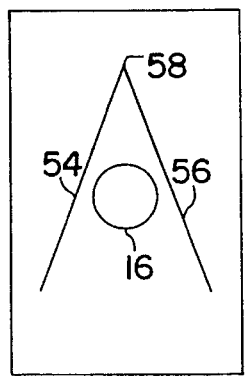
FIG. 6A is a top view of an alternate embodiment of the dressing of the present invention.
Figure 6B:
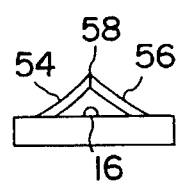
FIG. 6B is a side view of the dressing of FIG. 6A.

FIGS. 6A and 6B show a generally triangular shape for the incisions where the incisions 54 and 56 extend outwardly from point 58.

It will be appreciated by those skilled in the art that there are numerous incisions including the shapes of other polygons and even irregular shapes that may be made to conform the viewing area to the shape of the wound.

EXAMPLE 1

A dressing was prepared having two parts, a wound contact layer and an absorption component. The wound contact layer consisted of a hydrocolloid mass which was approximately 40 mils thick (0.0040 inch). Centrally located on the 5 inch×5 inch dressing was a hole approximately ½ inch in diameter. The hole extended the full thickness of the dressing. Exudate would pass through this hole into an absorbent component.

EXAMPLE 2

SUMMARY

An adhesive baseplate dressing, modified to contain a centrally located fluid vent and "access door" which permits wound access, covered by a Top Absorbent Dressing (TAD) remained intact for four (4) days on the porcine full-thickness wound model. The TAD was configured substantially as shown in FIG. 2 wherein the backing layer 28 was a polyurethane film, the adhesive 30 was DuoDerm CGF® hydrocolloid adhesive, the dressing element 24 was a superabsorbent pad laminate comprising a superabsorbent acrylic polymer in a cellulose matrix (commercially available as Salsorb®), and the non-stick film 32 was a bonded polypropylene film. The TAD controlled and prevented leakage of wound exudate for 24 hours. Leakage occurred from under the baseplate after 3 days without change to the TAD. The TAD was easy to apply and remove. After three (3) days, the TAD was removed, re-applied, and adhered well to the underlying baseplate.

Methodology

One (1), 5 way cross, Yorkshire swine, weighing approximately 20 kgs, received four (4) full-thickness excisions (2 wounds/flank) to the dorsal region on day O of the study.

Full-thickness excisional wounds were created with a No. 10 scalpel blade. Tissue was excised to the depth of muscle fascia and placed approximately 40 cm apart. Hemostasis was achieved using a gauze tamponade.

Following hemostasis, wounds were dressed with the Two Piece dressing. The baseplate which contained a centrally located fluid vent or "trap door" was positioned directly over the wound site and then covered by the TAD (Lot#NSPR-0273).

The two piece dressing was visually observed for leakage and photographed on post-op days 1 and 4. Only the TAD was changed and new dressings applied after 24 hours.

The test animal was sacrificed on day 4 of this study in accordance with the procedures outlined by the Department of Laboratory Animal Care.

Results

Visual Observations: No leakage of exudate was observed from under the TAD or the baseplate after 24 hours. Leakage did occur from under the baseplate after 3 days without change to the TAD. The TAD was easy to apply and remove without sticking to surgical gloves. The TAD could be removed and re-applied to the baseplate without dressing loss. Removal of the TAD showed the "trap doors" of the baseplate were resealed in the presence of fluid, but not distorted. These flaps could be re-opened with forceps in order to inspect the wound. The wound environment under the baseplate appeared moist on all observation days.

CONCLUSION

Heavily exudating wounds were managed by a hydrocolloid dressing that permits excess wound fluid to pass through a fluid vent or "access door", and become absorbed by a removable top dressing.

Thus, a hydrocolloid dressing can be used in a heavily exudative wound model which permits (1) contact of the granulation tissue with the hydrocolloid (2) visualization of the wound bed, and (3) extends wear time.

What is claimed is:

1. In a two piece wound dressing comprising an adhesive containing baseplate and means for absorbing excess wound exudate, the improvement wherein said baseplate includes:

at least one slit defining a flap which when lifted defines a first aperture suitable for first aperture and access and visualization; and, a second aperture substantially smaller than the dimensions of the wound adapted to provide direct exudate flow to said absorbing means.

2. The dressing of claim 1 wherein said baseplate has a pair of slits extending from said second aperture.

3. The dressing of claim 2 wherein said pair of slits define a straight line and have a further slit at each of their ends opposite said second aperture such that said pair of slits and said further slits form one or more flaps.

4. The dressing of claim 1 wherein said slit when released after viewing the wound forms an occlusive surface.

5. The dressing of claim 3 wherein an edge on one side of said slit adheres to an edge on the opposite side of said slit.

6. The dressing of claim 1 wherein said adhesive contains a hydrocolloid.

7. The dressing of claim 1 wherein said baseplate has at least two slits forming two or more sides of a polygon wherein the remaining side of said polygon is the imaginary line extending from the ends of the slits that form said polygon.

8. The dressing of claim 7 wherein said polygon is a rectangle.

9. The dressing of claim 7 wherein said polygon is a triangle.

10. The dressing of claim 1 wherein said adhesive is a pressure sensitive adhesive and has a thickness of about 0.001 to about 0.1 mil.

11. The dressing of claim 1 wherein said adhesive is a hydrocolloid, hydrogel, acrylic or polyurethane-based adhesive.

12. The dressings of claim 1 wherein said adhesive contains an antimicrobial or wound healing agent.

13. A wound pad comprising a dressing element comprising a polymer matrix including one or more absorbent and/or superabsorbent materials;

a non-stick film larger in size than said dressing element and overlying a wound-facing surface of said dressing element;

an adhesive layer larger in size than said non-stick film, said adhesive layer overlying a non- wound-facing surface of said dressing element;

wherein the area of said film beyond said element is adhered to said adhesive layer and wherein the area of said adhesive layer beyond said film provides adherence of said wound pad to a desired surface.

* * * * *